(12) United States Patent
Hesse

(10) Patent No.: US 9,005,103 B2
(45) Date of Patent: Apr. 14, 2015

(54) METHOD AND DEVICE FOR THE TREATMENT OF OVERWEIGHT

(75) Inventor: Albert Hesse, Wenden (DE)

(73) Assignee: Albert Hesse, Wenden (DE)

(*) Notice: Subject to any disclaimer, the term of this patent is extended or adjusted under 35 U.S.C. 154(b) by 286 days.

(21) Appl. No.: 12/894,861

(22) Filed: Sep. 30, 2010

(65) Prior Publication Data

US 2011/0105827 A1 May 5, 2011

(30) Foreign Application Priority Data

Oct. 1, 2009 (DE) .......................... 10 2009 043 728

(51) Int. Cl.
*A61N 2/02* (2006.01)
*A61N 2/04* (2006.01)
*A61F 5/00* (2006.01)

(52) U.S. Cl.
CPC ................ *A61N 2/02* (2013.01); *A61F 5/0003* (2013.01); *A61H 2201/10* (2013.01)

(58) Field of Classification Search
USPC .................................................. 600/9, 13, 14
See application file for complete search history.

(56) References Cited

U.S. PATENT DOCUMENTS

| 6,024,691 | A * | 2/2000 | Tepper et al. ................... 600/13 |
| 6,219,865 | B1 * | 4/2001 | Stokesbary ....................... 5/637 |
| 6,258,020 | B1 * | 7/2001 | Lopez .............................. 600/15 |
| 6,424,864 | B1 * | 7/2002 | Matsuura .......................... 607/3 |
| 6,652,445 | B1 * | 11/2003 | Woo ................................ 600/15 |
| 8,216,121 | B2 * | 7/2012 | Gleim et al. .................... 600/14 |
| 2005/0182287 | A1 * | 8/2005 | Becker ............................ 600/13 |
| 2006/0047325 | A1 | 3/2006 | Thimineur et al. |
| 2007/0250133 | A1 | 10/2007 | Carlson et al. |

FOREIGN PATENT DOCUMENTS

| DE | G 89 09 478.6 U1 | 12/1989 |
| DE | 199 63 908 A1 | 7/2001 |
| DE | 100 62 050 A1 | 4/2002 |
| DE | 203 03 835 U1 | 5/2003 |
| EP | 1 040 847 A1 | 11/1998 |
| WO | WO 97/46244 A1 | 12/1997 |

OTHER PUBLICATIONS

Walter Last, Magnet Therapy, http://www.health-science-spirit.com/magnet.html, retrieved on Nov. 25, 2013, backdated to May 6, 2004 via http://web.archive.org/web/20040506114854/http://www.health-science-spirit.com/magnet.html.*
"Thyroid Gland", http://dherbs.com/news/4823/4669/Thyroid-Gland/d,ai.html#VADbDPnwmh4, retrieved on Aug. 29, 2014, backdated to Sep. 15, 2008 via https://web.archive.org/web/20080915075202/http://www.dherbs.com/articles/thyroid-gland-37.html.*

* cited by examiner

*Primary Examiner* — Charles A Marmor, II
*Assistant Examiner* — Thaddeus Cox
(74) *Attorney, Agent, or Firm* — Norman B. Thot

(57) ABSTRACT

A device and a method of applying the device for the treatment of obesity or overweight in mammals, especially humans refers to a suitable substrate to be worn at the body of the patient and includes a thyroid stimulating pulsating magnetic field, whereby the magnetic field can be controlled and programmed as to the duration, frequency and pulsation of the magnetic field.

6 Claims, 5 Drawing Sheets

A

B

A

B

A

B

A

B

METHOD AND DEVICE FOR THE TREATMENT OF OVERWEIGHT

CROSS-REFERENCES TO RELATED APPLICATIONS

This application claims the priority of German Patent Application Serial No. 10 2009 043 728.2 filed Oct. 1, 2009, pursuant to 35 U.S.C. 119(a)-(d), the subject matter of which is incorporated herein by reference.

BACKGROUND OF THE INVENTION

The present invention relates to a method for the treatment of overweight and a device for carrying out the method.

Overweight, (obesity or adipositas) is a typical phenomenon of affluent societies. Typically, obesity is defined by an increase in body weight which is measured by such indices as the Broca-Index or computed by the body-mass-index (BMI). According to the WHO definition, obesity is present at a BMI of at least 30 $kg/m^3$.

Obesity is, at least in the western industrialized countries, a widespread disease. Almost every third adult citizen in Germany is obese and the numbers in other western countries are similar. Men are suffering sooner from the disease, that is, at a younger age; from the age of forty on those afflicted are predominantly women. In the last few years, it was found that more and more children are obese. This development is dangerous in as much as obese children have an increased risk to develop as adults nutrition dependent diseases such as high blood pressure, diabetes or coronary heart disease.

The negative consequences of obesity are varied and affect almost all organs, especially burdened are the heart and the lungs.

In obese persons, the heart must constantly work harder in order to supply the fatty tissue with sufficient blood flow. Moreover, there is more retention of water and sodium, which leads to high blood pressure and further burdens the heart. As a result, angina pectoris, coronary infarction or acute or chronic heart disease can follow. The lungs also have to work harder to supply the increased oxygen requirement. Oftentimes, the lung capacity is insufficient which results in chronic oxygen deficiency. These conditions are further aggravated by interference with breathing during sleeping, the so-called sleep apnea syndrome. Person, so afflicted complain about sleepiness during the day, loud snoring and restless sleep. Weight loss, almost completely alleviates these ailments.

Obesity is one of the most important risk factors for the onset of diabetes mellitus type 2.

Especially frequently occurring are fat metabolism disorders, that are accompanied by elevated levels of LDL, cholesterol and triglycerides that are dangerous for the heart/blood circulation system. In addition, there is the threat of fatty degeneration of the liver, gout and gall stones.

Obesity leads to stress on the joints, in particular, in the area of the spine, in the hip joints as well as the knee and ankle joints. Obesity accelerates their deterioration and leads to chronic pain that oftentimes can be treated only with pain killers or through surgery.

Obesity not only leads to bodily problems but can also manifest itself in mental problems. It can lead to low self esteem, isolation or depression that can, in a vicious cycle further lead to "binging attacks" and additional weight gain.

Obesity results only when the daily calorie intake over a long period of time exceeds that of the energy need of the body (positive energy balance). Today, it is believed that various other factors also play a role in the formation of obesity. Aside from eating behavior and the lack of movement, metabolic activity plays also a role in obesity.

In order to treat obesity, a variety of approaches exist that essentially rest on three pillars: nutrition, exercise and behavior therapy. However, these lead in only a small portion of the obese to a lasting weight loss. Among others, a lasting successful therapy requires considerable changes in lifestyle and eating habits of the patients. Many patients terminate the therapy prematurely, or post-therapy, they return to the old habits. This can result even in an increased weight gain, the so-called yo-yo effect.

In particularly difficult cases of adipositas, change in life style and eating habits have to be accompanied by medication or surgery, which oftentimes proves stressful on the patient.

In all therapy situations, compliance with the therapy by persons suffering from obesity is thus rather low.

From DE 100 62 050 A1 a method for the treatment of cellulite is known where a temporally variable magnetic field is applied to the surface of the body parts to be treated. It is also stated that this method can be applied in the treatment of obesity. To the person skilled in the art it remains however unclear whether and with what type of adaptations, a magnetic field therapy would be successful in the area of obesity.

It would therefore be desirable and advantageous to provide an improved method and/or device for the treatment of obesity to obviate prior art shortcomings and to provide the will to greater compliance in the patients. It would also be desirable to provide a method and/or device which can lead to permanent reduction of body weight, which is simple in application and is comfortable for a patient to comply with and/or is without side effects.

SUMMARY OF THE INVENTION

According to this aspect of the present invention, a device is provided for the treatment of adipositas; the device being in the form of a module producing a magnetic field that activates the thyroid of a mammal, especially a human patient having adipositas. Such a device includes a generator module for the generation of a magnetic field and a control unit that can be attached closely to the body of a mammal or a patient. The generator module produces a pulsating magnetic field preferably of a frequency of from 3 to 60 Hz, preferably a frequency of 7 to 20 Hz, especially preferred of a frequency of 14 Hz.

The magnetic field of the device increases the thyroid activity in a patient thus leading directly to the weight reduction in the patient. At the core of the invention is the utilization of a magnetic field for the purpose of weight reduction in adipositas patients.

The magnetic field is a pulsating magnetic field and the control of the pulsation according to the present invention is preferably electronic and not mechanical, for example, by using a switching circuit. As compared to a mechanical control, which could be for example, a rotating permamagnet, the electronic control has the advantage of a much lower noise level and a reduced energy use which leads to a longer life expectancy of the device. Preferably, the device is free of permamagnets, such that in the "off" mode of the device, no magnetic field is being generated and thus any undesired effects avoided. It is further preferred that the device, aside from any impact resulting from the attachment of the device to the body, no other mechanical stresses accompany the attachment of the device to the surface of the body, in particular, the attachment to the thyroid, and to so prevent irritations due to mechanical forces.

The module that generates the magnetic field according to the present invention is housed in the device, which is preferably designed for close attachment to the body of the patient, so that activation of the thyroid can be carried out in optimal manner. The scope of the activation or the amount of the activation is adjustable via the size of the module, the length of application, the force of the magnetic field and/or the properties of the magnetic field.

The thyroid gland is the organ in the human body that decisively controls the metabolic activity via the production of iodine containing hormones. The thyroid, in Latin glandula threoiea is a hormonal gland, which in humans, is situated at the neck below the larynx in front of the trachea. In humans, the organ has the shape of a butterfly.

The main function of the thyroid gland, aside from the storage of iodine, is the formation of the iodine containing thyroid hormone thyroxine, tetra iodothyronine, (T4) and triiodothyronine (T3). The iodine containing thyroid hormones are formed by the follicle epithelial cells of the thyroid gland (thyrozytes) and regulate the metabolism and functional condition of almost all organs. The thyroid hormones are part of the so-called thyrotropic regulation circuit. The function of the thyroid is thus controlled by the hypothalamus and the pituitary gland. In the pituitary gland the hormone TSH (Thyroid Stimulating Hormone) is formed and released into the blood circulation. When reaching the thyrozytes, it enhances their growth and the release of T3 and T4. These hormones thus released from the thyroid, have an effect on the heart and the circulation and lead to an increase in heart frequency, blood pressure and vasodilation. In addition these hormones have an effect on the metabolism of sugar, fat and connective tissues.

Through the effect of the thyroid hormones, the energy expenditure and the metabolism of the organism are regulated. It is known that a thyroid under function, hypothyroidism, often leads to overweight while thyroid hyperfunction, hyperthyroidism, leads to underweight. The present invention incorporates the connection between a thyroid hyperfunction and the often corresponding underweight of the patient, by activating the thyroid through a magnetic field, in order to induce weight loss.

One of the remarkable features of the process according to the invention is that the weight loss that is induced through the increase in the thyroid function, basically is not accompanied with the problematic symptoms that often accompany the pathological hyperfunction of the thyroid, such as for example increased heart rate, tremors or sleeplessness. Application of a magnetic field has the special advantage to reach a rather moderate activation of the thyroid, which does not induce a critical hyperfunction of the thyroid with any unwanted consequences. An "overdose" of this magnetic field therapy is accordingly per se ruled out. Side effects can therefore be at least mostly avoided.

Within the scope of the present invention, the activation of the thyroid is commensurate with the increase or stimulation of the thyroid activity. The thyroid activity is illustrated by means to the blood values of the patient with respect to the free T3 (fT3) or T4 (fT4). The thyroid activity can also be determined by the blood value of TSH.

An increase in the thyroid activity is detectable when the fT3 and fT4 values of the patient increase to more than the patient's individual baseline value. At a normal value in all humans of 0.89 to 1.70 ng/dl in blood (serum) for fT4 and 2.0 to 4.2 pg/ml in blood for fT3, the individual fluctuation range in humans for fT4 and fT3 is normally at 1-2%. Circadian and seasonal fluctuations of these hormones are not observed. Accordingly an increase of 2% of each of the individual starting values as activation of the thyroid is within the scope of the present invention.

The reduction of the individual TSH blood values can also serve as an indicator for the activation of the thyroid. This value in humans is generally about between 0.35 and 2.50 µIU/ml. The individual fluctuation here is also at about 1-2%. In accordance with the present invention, a reduction below 2% of the individual starting value, counts as indirect indicator for the activation of the thyroid in accordance with the invention.

This activation of the thyroid by means of the process or application of the device according to the present invention is particularly suited for treating patients with an adipositas degree I, that is, patients with a BMI of 30 to 34.9 kg/m$^2$, or degree II that is, patients with a BMI of 35 to 39.9 kg/m$^2$. However, patients with an adipositas degree III, that is patients with a BMI of at least 40 is also possible, in particular in these severe cases, a combination with other therapeutic actions is highly recommended.

The device according to the present invention has the advantage that it can induce a weight reduction in the adipositas patient without the patient changing or varying its general life style—exercise—or eating habits. The patient can thus continue a normal life and work simultaneously on the goal of weight loss either because of medical reasons and/or aesthetic reasons.

The device according to the present invention can be applied in nearly all life situations, for example during a work related activity, while resting or during sports activities, at home or when traveling. This becomes essential especially for long term application. The device according to the present invention and the process thus lead to an improved compliance with the therapy in the patient because of a comfortable application.

The device has the advantage that it can be utilized and applied by persons not having medical background. Thus, the patient can attach the device to the body of the patient without assistance from medically trained personnel and can activate the generator module. The device according to the present invention permits a simple application.

The device is not only suited for the treatment of obese humans but also can be used on animals that have similar problems, since obesity, especially in house pets such as dogs and cats, is also a problem.

The device according to the present invention can be configured for close to the body wearing, that is, either wearing it directly at the body of the patient (human or animal) or at or in the clothing or equipment (harness i.e. halter) which are worn at the body. The generator module generating the magnetic field should preferably be disposed in the device for positioning at or directed at the thyroid or also the neck of the patient during the application of the device.

The generator module can be adjusted to the size or shape of the thyroid. Thus, the generator module, for example, can be fashioned in the shape of a butterfly. In a preferred embodiment, the maximum size of the body surface of the neck is maximally 200 cm$^2$, preferably maximally 150 cm$^2$, especially preferred maximally 100 cm$^2$ or maximally 50 cm$^2$.

In one embodiment, the device is configured as a flat support, for example as a neck band, neckerchief, scarf, shawl or a neck brace or neck support. In this manner, a possibly largest contact surface between the neck region of the patient and the generator module of the device is realized. The module can be supported by the support or it can be integrated into the support. Likewise, an attachment can be onto or can be integrated into equipment such as clothing, for example jackets, coats or vests.

The device can also be directly attached to the skin. In this case, the support can be configured as a patch.

The device can also be integrated into accessories, or it can form an accessory, for example a piece of jewelry, a head band, a collar, and a veil or similar.

The attachment of the device at the body can be realized in any known ways. Accordingly, the configuration of the device can include attachment elements, for example, rivets, buttons, toggles, bands, buckles, hooks, zippers or hook and loop closures.

The device according to the present invention can be constructed as a textile product, for example, as a woven or knitted fabric, as a felt or milled fabric, or non-woven web or formed fabric. Advantageously, these textiles are flexible and thus may optimally and individually adapt to the body area to be treated. When the device is constructed in a flat shaped embodiment, it improves the wearing comfort and adjustment of the patient with the positive effect that it will enhance the therapy compliance of the patient.

In one embodiment, the device itself can be a piece of clothing or at least a portion thereof. The piece of clothing can have corresponding adjustment elements such as a hook and loop closure or a strip of buttons or similar, by which the device can be individually adjusted to each patient.

The single constituents of the device can be chosen as light weight as possible with a view toward the utmost comfort for the patient.

The electronic constituents of the device, such as for example, the generator module, cables or electronic control can be attached at the device and need not represent separate parts of the device, that is, they are integrated into the device and not detachable without destroying the device. Any one or more of the electronic constituents can be integrated into the device in this manner.

It is also possible to configure the device so that the electronic constituents are detachable from the device without causing its destruction. This would be advantageous for exchanging single constituents or replace them for repair.

The electronic constituents of the device can be either in whole or in part applied at the patients clothing or accessories. In an advantageous embodiment, the components can be applied in an invisible manner so they cannot be spotted by others, for example in the inner lining or inner pocket of a jacket, in a muffler or scarf, or in the knot of a tie or a bow tie, or the part can be itself in the form of an accessory.

The device can send out acoustical, optical or tactile signals including vibration signals that indicate certain functional conditions, for example, indicating the state of charge, indicating an interference or signaling the end of the treatment period. It can also serve to remind the user of certain action to be taken, such as for example, to attach the device or to remove the device.

To supply the device with energy, batteries can be utilized, preferably of the size A, AA or button batteries, also those batteries that can be recharged. Alternatively, other current producing devices, such as solar cells or miniature wind generators can be utilized.

The generator module, as afore-stated emits a pulsating magnetic field.

In one embodiment the pulsating magnetic field has a frequency of 1 Hz to 100 Hz, preferably 7 to 20 Hz and especially preferred a frequency of 14 Hz.

It has been shown that the use of a pulsating magnetic field as compared to a static magnetic field has great importance for the success of the method according to the present invention. Especially good results are realized with frequencies of the pulsating magnetic field in the range of about 7 to 20 Hz and in particular, at about 14 Hz. Success according to the present invention can also be realized at frequencies which range from about 3 Hz to about 60 Hz. For example, it is possible, in accordance with the present invention, to adjust the frequency of the pulsating magnetic field to a Schumann-resonance frequency.

The device according to the present invention is especially preferred when comprising a generator module for generating a magnetic field and a control unit and is attachable close to the body of the mammal and wherein the generator module is capable of producing a pulsating magnetic field with a frequency in the range from 1 Hz to 100 Hz, preferably 7 Hz to 20 Hz and especially preferred with a frequency of 14 Hz.

The flow density of the magnetic field can be in the range of 0.1 to 100 µT. Optionally, the flow density is time dependent, for example, by an exponential increase and/or decrease.

In one embodiment of the present invention, the impulse form of the magnetic field is illustrated by a simple wave function, especially preferred as a sinus curve, as a rectangular curve, a trapezoidal curve or a saw tooth curve. Optionally, the impulse form, that is the pulsation of the magnetic field, is temporally changeable, that is, during the period of application the magnetic field can be changing.

The period of applying the method of the present invention, or the duration of the treatment with the device according to the present invention can be determined individually and can extend for a period of days up to weeks and months. A continuous treatment is also possible, which will, as the case may be, interrupted only by periods of sleeping. A daytime application can be varied likewise in individual manner, and can be one time or several times a day. An application cycle can last, for example, from several minutes to several hours. The device can comprise a control unit which allows individual programming for an individualized application plan.

The device according to the present invention is controllable relative to the properties of the magnetic pulsation with respect to strength, frequency and/or form of pulsation and is adjustable to the duration of treatment, frequency and duration of a single application to concrete, individual therapeutic requirements. In a suitable embodiment, these properties can likewise be individualized via the control unit and programmed in corresponding manner.

The application of the method according to the present invention can be supported with the intake of food supplements. Preferred are polyphenol-rich polyphenol and aromatic compounds with two or more hydroxyl groups that are directly bound to the aromatic ring such as attributed to secondary plant stuffs. Polyphenols are contained in plants, which are rich in antioxidants and thus support health. Examples of polyphenol rich foods are appleberries, red grapes, red wine, mangosteen (*gracinia mangostana*), pomegranates (*punica granatum*), gingko, tea in particular, green tea, zistroses, the seeds of perilla (*perilla frutescen*), chinese lemon balm, turmeric. Within the scope of the present invention, polyphenol is defined as isolated or chemically synthesized polyphenol. Examples of isolated polyphenols are Quercetin or Resveratrol. The device according to the present invention and its application are thus suitable for a combination with the above identified agents.

In an especially preferred embodiment of the present invention, the device is configured as a neck band which includes an actuating generator module for generating a magnetic field, an electronic control and an exchangeable energy supply. It is preferred to utilize one or more coils for the generator module.

DEFINITIONS

"Neck band" within the scope of the present invention is a flat support in band or string shape for placing around the neck.

The term "Generator module" is any device which is capable of generating a static or pulsating magnetic field. A static magnetic field can be generated by one or more permamagnets or an electric magnet without a pulsating flow of current. Advantageously, a pulsating magnetic field includes a generator module of one or more coils of current conducting material such as for example, copper wire.

The term "pulsating magnetic field" within the scope of the present invention, is generally a magnetic field that changes over time and whose intensity during the passage of time includes more than one local maximum. For example, exponentially increasing and/or exponentially decreasing pulses are possible. The pulsating magnetic field is preferably one that is characterized by periodically varying magnetic fields also known as magnetic pulsations, by frequency, impulse form and strength.

The term "patient" within the scope of the present invention is a mammal, in particular a human.

"Treatment" within the scope of the invention means any action which aids in preventing, easing or healing a disease in a patient.

EXAMPLES

Eight female and two male patients with marked thyroid hypofunction and light to severe adipositas—degree 2-3 were treated with the method according to the invention during a period of four weeks, wherein the pulsating magnetic field had a frequency of 14 Hz, with sinus oscillation and a magnetic flow density of 50 µT, twice daily for 30 minutes each. The normal daily habits of the patients such as nutritional uptake, exercise and sleep pattern were unchanged. At the start and at the end of the treatment period, the blood values for the thyroid stimulating hormone TSH (thyroid stimulating hormone) and the thyroid hormone fr3 and fT4 that are present in free from were determined. In addition, the level of selenium in the blood and the weight of the patient were recorded.

Results

In the overwhelming majority of the patients, changes in the level of TSH, fT3 and fT4 which are a characteristic of the thyroid activity were found. The level of TSH decreases as seen in Table 1 for patients No. 1-3 and FIGS. 2A and 2B for patients 4 to 14, whereby the emission of TSH produced in the pituitary gland is inhibited by the thyroid hormone fT3 and fT4. This inhibition is the result of negative feedback within the scope of the thyrotropic control circuit via the reduced production and emission of TRH from the hypothalamus. As expected, in corresponding manner an increase of plasma concentration of fT3 and fT4 in almost all patients was observed, as seen in Table 2 and FIGS. 3 and 4. During the same time period, the level of concentration in TSH decreased.

In laboratory tests, the selenium level in the blood was determined at the same time. Selenium plays an important role in the production of the thyroid hormone, more exactly, in the "activation" of thyroxine (T4) to triiodothyronine (T3). Selenium is a constituent of an enzyme of the thyroxin-5'-deiodinase, responsible for the removal of an iodine atom of T4. Through the de-iodination T3 results. Selenium deficiency leads to a lack of thyroxin-5'-deiodinase and thus to a T3 deficiency.

During the treatment with the device according to the present invention ("thyreogym-treatment") no measurable change in the level of selenium was recorded as seen in FIG. 5.

TABLE 1

Tabulated compilation of the measured plasma concentration of TSH (hypersensitive), free thyroxin (fT4 and free triiodothyronine (fT3). The measurement was taken prior to ("prior") and after a four week treatment period ("post") with the method of the present invention. The treatment was carried out two times daily, each for 30 minutes. The magnetic field was 14 Hz.

| | Patient #10 | | Patient #9 | | Patient#2 | |
|---|---|---|---|---|---|---|
| Hormone | before | after | before | after | before | after |
| TSH(µIU/ml) | 2.22 | 1.22 (−45.0%) | 2.48 | 2.24 (−9.7%) | 2.12 | 1.94 (−8.5%) |
| fT4 (ng/dl) | 0.92 | 1.1 (+19.6%) | 0.89 | 0.96 (+7.9%) | 0.97 | 1.13 (+16.5%) |
| fT3 (pg/dl) | 2.6 | 2.8 (+7.7%) | 2.1 | 2.4 (+14.3) | 2.2 | 2.5 (+13.6) |

The measurement of the body weight showed a weight reduction in the range from 4 to 10 kg.

Side effects were not observed.

Evaluation of the Study Results

The method leads unequivocally to an activation of the thyroid gland, as determined by the corresponding control of the essential hormone fT3, fT4 and TSH of the thyrotropic circuit. The weight reduction accompanying the application thus explains the activation of the thyroid gland. It is important that the growth in the free thyroid hormone occurs in moderation, so that side effects which usually accompany a thyroid activation induced by drugs do not occur.

Comparative Example

Three female patients with light to severe adipositas—degree 2-3 (patients 15-17) were treated in a time period of four weeks with a method, as afore-described, except that instead of a pulsating magnetic field, a static magnetic field was employed. The normal habits of the patients such as nutritional uptake, exercise or sleeping pattern remained unchanged. The blood values for TSH and fT3 and fT4 in the patient were determined in the beginning and the end of the treatment period.

| | Patient #15 | | Patient #16 | | Patient #17 | |
|---|---|---|---|---|---|---|
| Hormone | before | after | before | after | before | after |
| TSH(µIU/ml) | 3.74 | 3.72 (−0.5%) | 10.47 | 10.50 (+0.3%) | 0.69 | 0.68 (−1.4%) |
| fT4(ng/dl) | 1.23 | 1.2 (−2.4%) | 1.30 | 1.30 (+/−0%) | 1.30 | 1.30 (+/−0%) |
| fT3 (pg/dl) | 2.7 | 2.7 (+/−0%) | 2.6 | 2.8 (+7.7%) | 2.5 | 2.6 (+4.0%) |

The comparative example shows that the values of TSH, fT4 and fT3 are not significantly changed when a static magnetic field instead of a pulsating magnetic field was used in those patients. Even the body weight of the patients after treatment are not significantly different from that before the treatment. Accordingly, to realize success with the method according to the present invention, the application of a pulsating magnetic field is therefore essential.

The present invention will be more readily apparent by way of an embodiment.

Detailed Description of Preferred Embodiments

Throughout all the Figures, same or corresponding elements are generally indicated by same reference numerals.

In FIG. 1, there is shown a schematic illustration of the device according to the present invention for an application of weight reduction in the form of a neck band.

The embodiment as shown in FIG. 1 is a device for generating magnetic pulsations and is configured in the form of a flexible padded neck band 2. The neck band 2 has attachment elements 1, 9, for example, snap buttons or hook and loop closure for closing the device around the neck 3 of a patient 10. Furthermore, the neck band 2 is provided with an electronic control 4 (which is preferably in the form of a plate and disposed in an easily accessible pocket). The control unit 4 includes one or more coils 5 for generating a pulsating magnetic field. An actuating element 6 for controlling the electronic control 4 and a connecter cable 7 are also provided, as well as an exchangeable energy supply 8, (such as a replaceable battery is provided and tucked into a closeable compartment) at the neck band 2.

The patient 10 shown here schematically illustrates the disposition of the device at the neck 3 of the patient. To improve the wearing comfort, the neck band 2 is provided with a chin cavity to mold around the chin of the patient 10. Preferably, the device 2 includes that control elements are disposed at the device, not shown here in detail; such as an on/off switch or means for the adjustment of the magnetic field, that is, for adjustment of the parameters of the magnetic field (for example, control of the time of day the device is switched on, the duration of the application and/or various cycles. There is likewise a control for the magnetic field intensity, or flow density, a control for the pulsations of the magnetic oscillations and a control for the frequency of the magnetic pulsations).

Figure 1:
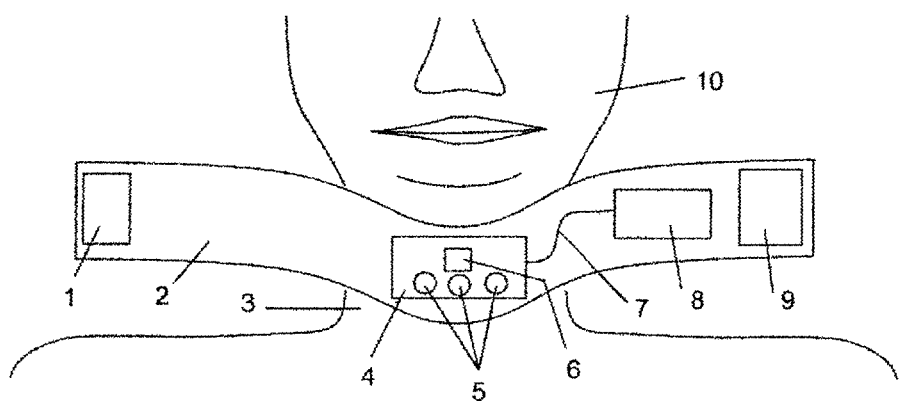
Figure 2:
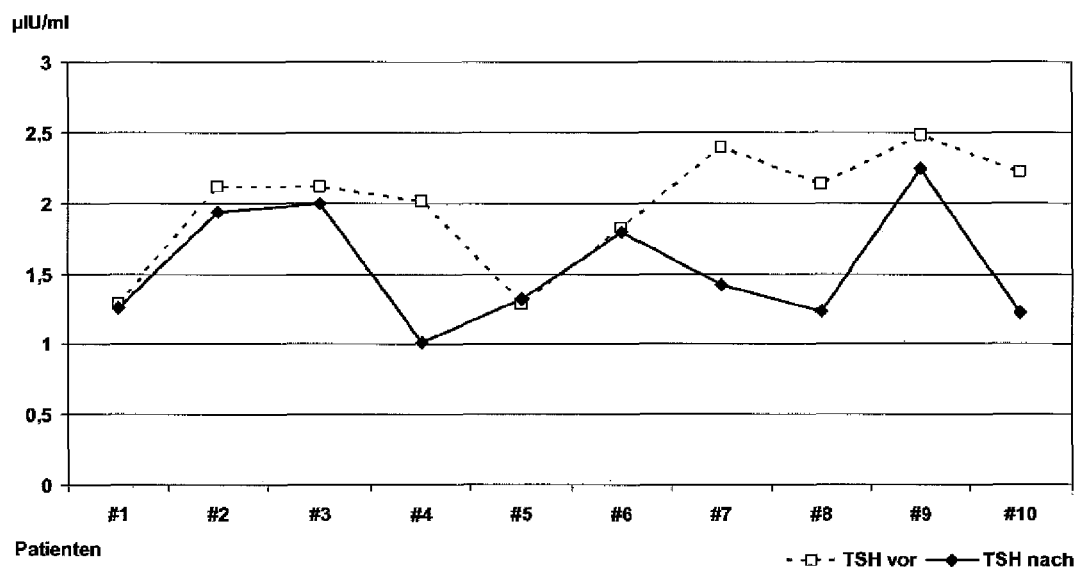
FIG. 2A shows a line graph and FIG. 2B shows a bar graph of the concentration of the TSH in the blood of the patients before and after the thyreogym treatment, wherein TSH/l of blood is measured in µg.
Figure 2:
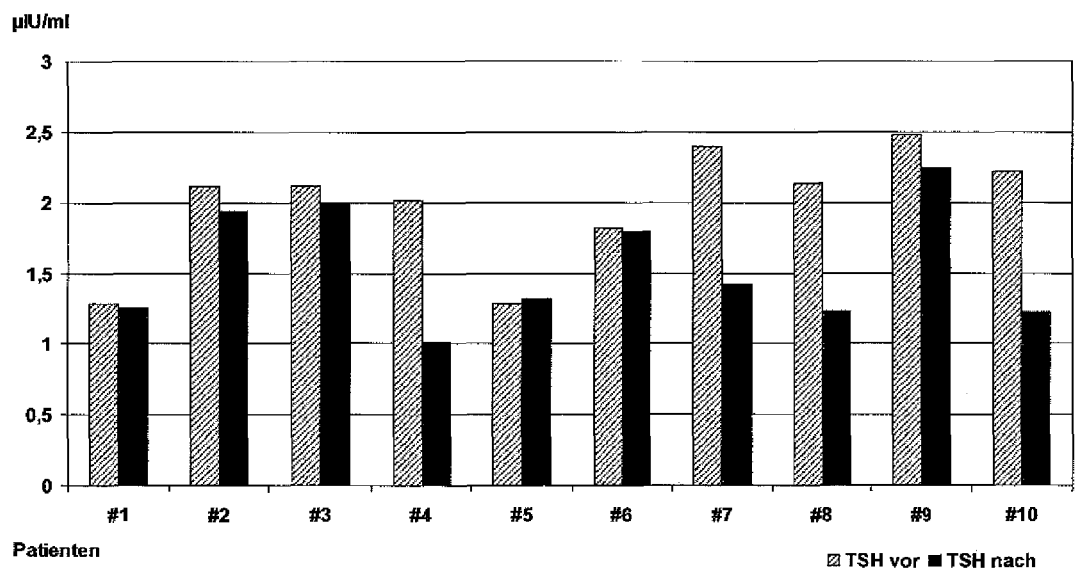
Figure 3:
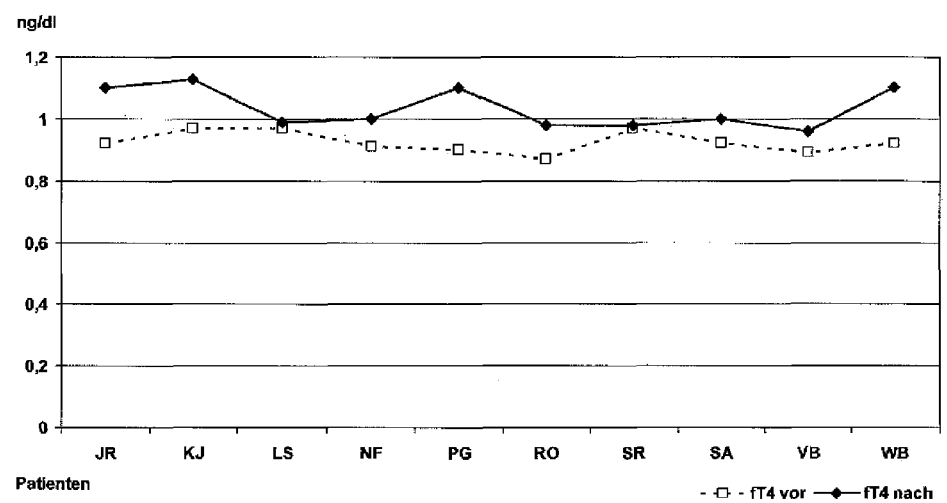
FIG. 3A shows a line graph and FIG. 3B shows a bar graph of free T4 in the blood of the patients before and after the thyreogym treatment wherein the fT4/dl of blood is measured in ng.
Figure 3:
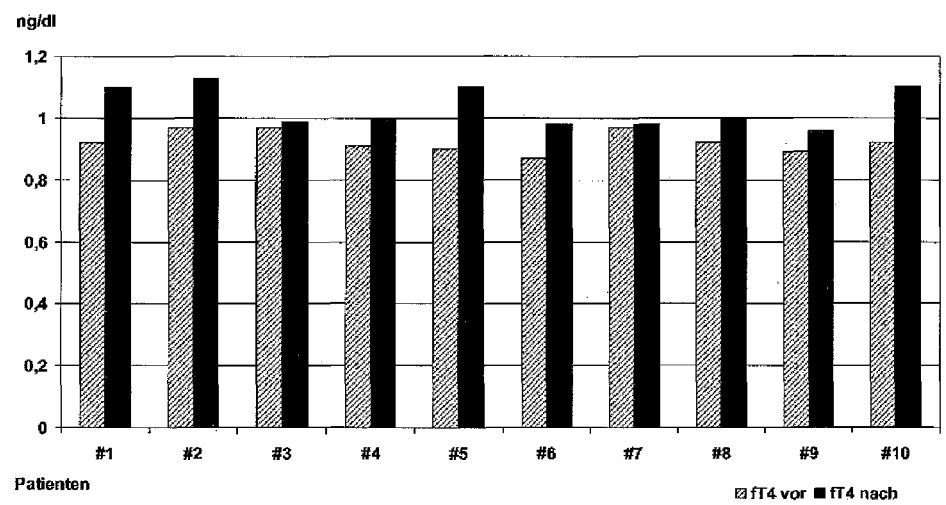
Figure 4:
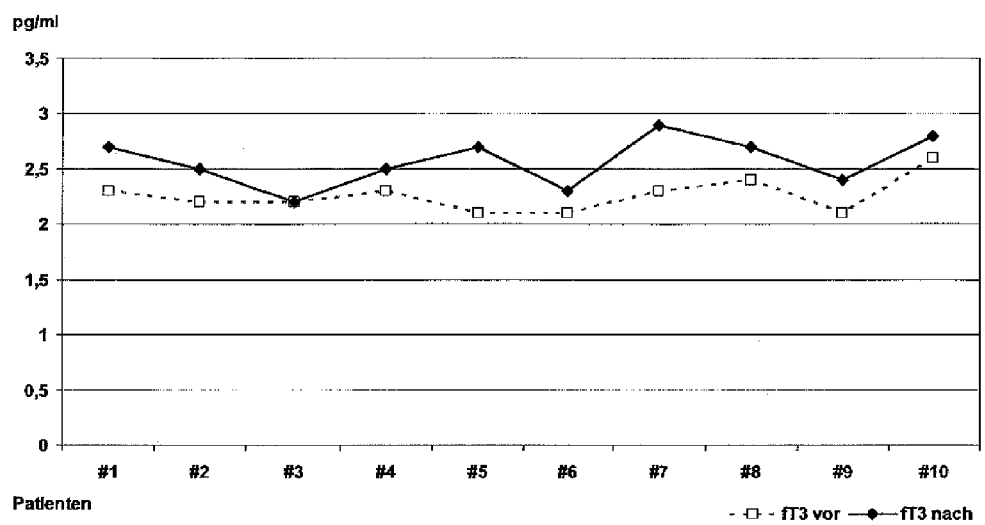
FIG. 4A shows a line graph and FIG. 4B shows a bar graph of free T3 in the blood of patients before and after the thyreogym treatment wherein the fT3/ml of blood is measured in pg.
Figure 4:
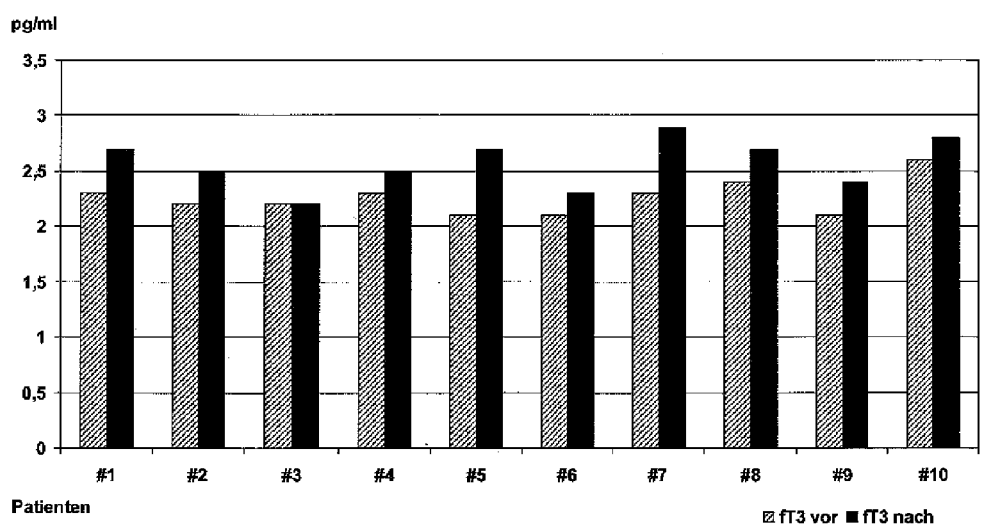
Figure 5:
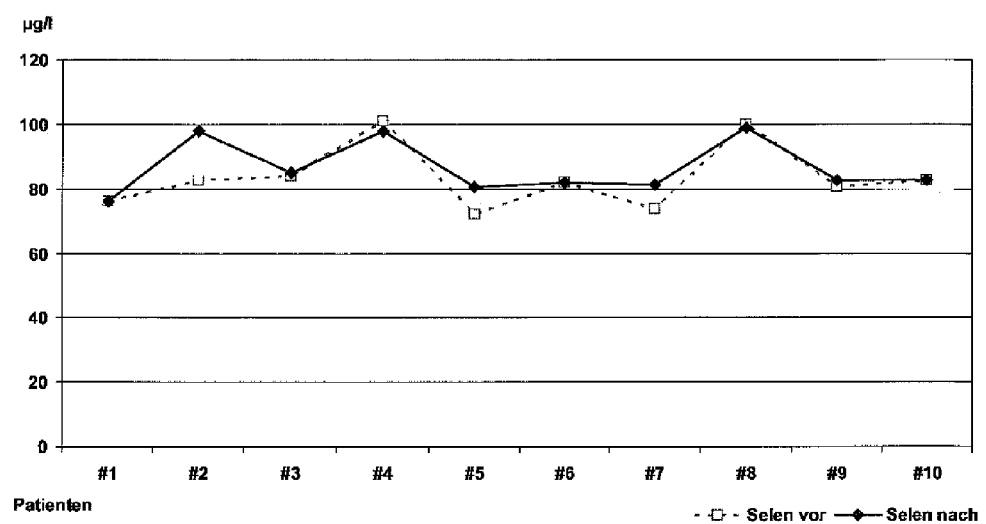
FIG. 5A shows a line graph and FIG. 5B shows a bar graph of selenium in the blood of the patients before and after the thyreogym treatment wherein the selenium/l of blood is measured in µg.
Figure 5:
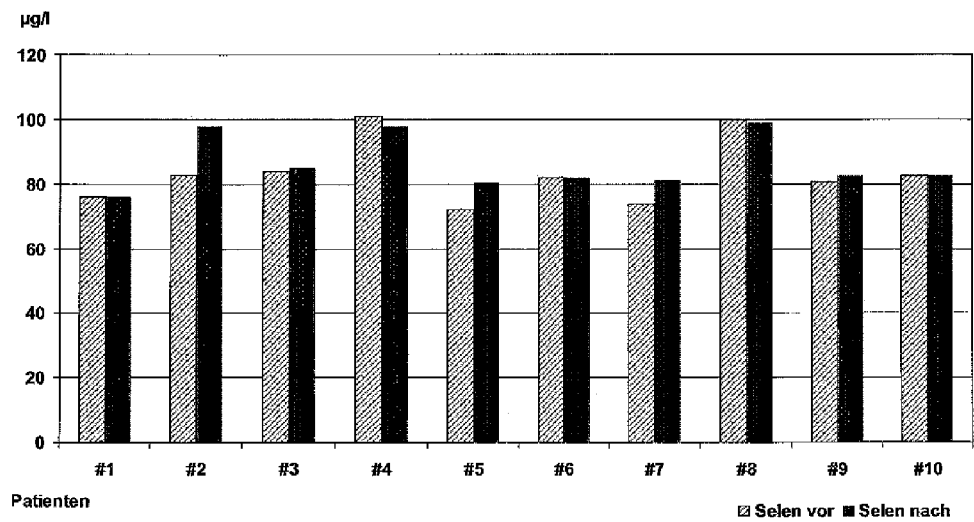

What is claimed is:

1. A method of treating obesity in a subject, the method comprising:
    applying a pulsating magnetic field with a single frequency selected from a range of from 7 Hz to 20 Hz and a field strength selected from a range of from 45 to 55 µT to a thyroid area of the subject,
    wherein,
    the applying of the pulsating magnetic field occurs for at least one application cycle of from several minutes to several hours for a treatment period of from days to months, and
    a free T3 blood value and a free T4 blood value of the subject is increased so that the subject thereby realizes a weight loss.

2. The method as recited in claim 1, wherein the at least one application cycle is twice daily for approximately 30 minutes each.

3. The method as recited in claim 1, wherein the free T3 blood value and the free T4 blood value are each increased by ≥2%.

4. The method as recited in claim 1, wherein a TSH blood value of the subject is reduced by <2%.

5. The method as recited in claim 1, wherein a form of the pulsating magnetic field is selected from the group consisting of a sinusoid, a rectangular curve, a trapezoidal curve and saw tooth curve.

6. The method as recited in claim 1, wherein the single frequency is 14 Hz.

* * * * *